United States Patent [19]
Herbig et al.

[11] Patent Number: 5,603,953
[45] Date of Patent: Feb. 18, 1997

[54] SUPPORTED LIQUID MEMBRANE DELIVERY DEVICES

[75] Inventors: Scott M. Herbig; Kelly L. Smith, both of Bend, Oreg.; Paul Van Eikeren, Carlisle, Mass.; James B. West, Bend, Oreg.

[73] Assignee: Pfizer Inc., New York, N.Y.

[21] Appl. No.: 424,511

[22] Filed: May 23, 1995

Related U.S. Application Data

[63] Continuation of PCT/US93/07463, Aug. 12, 1993, which is a continuation of Ser. No. 982,815, Nov. 30, 1992, abandoned.

[51] Int. Cl.$^6$ .............................. A61K 9/30; A61K 9/32; A61K 9/36; A61K 9/22
[52] U.S. Cl. .................. 424/473; 424/451; 424/463; 424/475; 424/480; 424/482; 424/489; 424/494; 424/497; 424/468; 514/772.3; 514/773; 514/784; 514/785
[58] Field of Search ..................................... 424/473, 482, 424/451, 463, 475, 480, 489, 494, 497, 468

[56] References Cited

U.S. PATENT DOCUMENTS

| | | | |
|---|---|---|---|
| 3,952,741 | 4/1976 | Baker | 128/260 |
| 3,965,255 | 6/1976 | Block et al. | 424/472 |
| 4,016,880 | 2/1983 | Theeuwes et al. | 128/260 |
| 4,183,960 | 1/1980 | Asher et al. | 424/946 |
| 4,201,691 | 5/1980 | Asher et al. | 435/2 |
| 4,657,543 | 4/1987 | Langer et al. | 604/891 |
| 4,762,899 | 8/1988 | Shikinami | 528/49 |
| 5,026,342 | 6/1991 | Hammersledt et al. | 435/2 |
| 5,034,317 | 7/1991 | Arnost et al. | 435/18 |

FOREIGN PATENT DOCUMENTS

| | | |
|---|---|---|
| 0162492 | 11/1985 | European Pat. Off. |
| 0357369 | 3/1990 | European Pat. Off. |
| 0467488 | 1/1992 | European Pat. Off. |
| 0485840 | 5/1992 | European Pat. Off. |
| 2599270 | 12/1987 | France |
| 9202212 | 2/1992 | WIPO |
| 9205775 | 4/1992 | WIPO |

OTHER PUBLICATIONS

Yoshitomi, H., et al. "Evaluation of Enteric Coated Tablet Sensitive to Pancreatic Lipase.I. In vitro Disintegration Test" *Chem. & Pharm. Bull.*, vol. 40, No. 7, Jul. 1992.
Takenchi, et al., *J. Membrane Sci.*, 42, 1989, pp. 183–188.
Pitt, et al., *Chem. and Life Sci.*, pp. 363–374 (1985).
H. Brondsted, et al., *Proceed. Intern. Symp. Control. Bel. Biact. Mater.*, vol. 17, pp. 128–129 (1990).
H. Takeuchi, et al., *J. Membrane Sci.*, vol. 34, pp. 19–31 (1987).

(List continued on next page.)

*Primary Examiner*—James M. Spear
*Attorney, Agent, or Firm*—Peter C. Richardson; Gregg C. Benson; A. Dean Olson

[57] ABSTRACT

Supported liquid membrane delivery devices that release a beneficial agent to an aqueous environment following exposure to an environmental trigger. A microporous hydrophobic support membrane at least partially surrounds a beneficial agent- containing hydrophilic formulation. A hydrophobic liquid is held within the microporous support membrane by capillarity and the hydrophobic liquid is substantially permeable to the aqueous environment and the beneficial agent-containing hydrophilic formulation. The entrained hydrophobic liquid becomes substantially permeable to the aqueous environment upon exposure to an environmental trigger such as an enzyme, and the beneficial agent is subsequently released.

21 Claims, 2 Drawing Sheets

OTHER PUBLICATIONS

J. Heller and S. H. Pangburn, "Proceedings of the 13th International Symposium on Controlled Release of Bioactive Materials", SRI International, pp. 35–36 (1986).

S. Ueda, et al., *Proceed. Intern. Symp. Control. Rel. Bioact. Mater.*, vol. 15, pp. 450–451 (1988).

A. Rubinstein, et al., *Proceed. Inter. Symp. Control. Rel. Bioact. Mater.*, vol. 17, pp. 466–467 (1990).

S. W. Shalaby, et al., *Proceed. Intern. Symp. Control. Rel. Bioact. Mater.*, vol. 17, pp. 134–135 (1990).

J. D. Way, et al., *J. Membrane Sci.*, vol. 12, pp. 239–259 (1982).

Y. H. Bae, et al., *Proceed. Intern. Symp. Control. Rel. Bioact. Mater.*, vol. 15, pp. 312–313 (1988).

G. Smets, *J. Polym. Sci.*, vol. 13, pp. 2223–2231. (1975).

J. Heller, et al., *J. Appl. Polym. Sci.*, vol. 22, pp. 1991–2009 (1978).

P. R. Danesi, et al., *J. Membrane Sci.*, vol. 31, pp. 117–145 (1987).

B. S. Kim and P. Harriot, *J. Collid. Interface Sci.*, vol. 115, pp. 1–8 (1987).

H. P. Merkle, et al., "Advances in Drug Delivery Systems", Anderson and Kim (eds.) Elsevier, Amsterdam pp. 99–111 (1986).

J. Heller and J. Kost (ed.) "Pulsed and Self Regulated Drug Delivery", CRC Press, Boca Raton, FL, pp. 93–108 (1990).

E. Mathiowitz, et al. *Reactive Polymers*, vol. 6, pp. 275–283 (1987).

J. Kost (ed.), "Pulsed and Self–Regulated Drug Delivery", CRC Press, Boca Ration, FL, pp. 3–16 (1990).

J. D. Gresser and J. E. Sanderson, "Biopolymeric Controlled Release Systems", CRC Press, Boca Raton, FL, vol. II, pp. 127–138 (1984).

SUPPORTED LIQUID MEMBRANE DELIVERY DEVICES

This application was filed under 35 U.S.C. §371 based on PCT/US93/07463, which was filed on Aug. 12, 1993 which is a continuation of U.S. application Ser. No. 07/982,815 which was filed on Nov. 30, 1992 and is now abandoned.

BACKGROUND OF THE INVENTION

This invention relates to devices useful for the delivery of a beneficial agent to an environment of use.

There are many devices in which exogenous agents (triggers) such as enzymes, enzyme substitutes, antibodies, heat, light, nucleophiles and changes in pH interact with a device release barrier such as a coating or matrix in such a way as to remove the barrier and consequently release the active ingredient. For example, there are polymeric membrane delivery systems which, in response to external stimuli, undergo a change in permeability, or a change in erosion rates (Pitt, C. G., Z.-W. Hendren, Z-W., J. Thompson, and M. C. Wani, "Triggered Drug Delivery Systems," in Advances in Drug Delivery Systems, Anderson and Kim (eds.), Elsevier, Amsterdam (1985) p. 363; Heller, J. and S. H. Pangburn, S. H., "A Triggered Bioerodible Naltrexone Delivery System," in Proceedings of the 13th International Symposium on Controlled Release, 1986 p. 35). In both cases the physical or chemical nature of the polymeric membrane itself is altered in response to the trigger.

In addition, osmotic-bursting systems have been developed that are initiated in the presence of water and thus are "triggered" upon ingestion or in a humid environment (Ueda, S., R. Ibuki, Hata, and Y. Ueda, "Design and Development of Time-controlled Explosion System (TES) as a Controlled Drug Release Systems," Proceed. Intern. Syrup. Control. Rel. Bioact. Mater., 15 (1988) 450; Baker, U.S. Pat. No. 3,952,741; and Theeuwes and Damani, U.S. Pat. No. 4,016,880).

Another common trigger for drug release is solution pH (e.g. enteric coatings). For example, enteric coatings consisting of cellulose acetate phthalate, resist action of duodenum fluids, but readily disintegrate in the ileum. (Remington's Pharmaceutical Sciences, J. E. Hoover, ed. Mack Publishing Co., Easton, Pa. (1970) pp 1689–1690).

Temperature triggered systems include hydrogels of N-isopropylacrylamide (NIPA) and other n-alkyl acrylamides that swell and contract in response to different temperatures (Hoffman, A. S., "Application of Thermally Reversible Polymers and Hydrogels in Therapeutics and Diagnostics," in Advances in Drug Delivery Systems, 3, Anderson and Kim (eds.), Elsevier, Amsterdam (1987) p. 297; Bae, Y. H., K. Mukae, K., T. Okano, and S. W. Kim, "On-Off Transport Regulation through Thermosensitive Hydrogels," Proceed. Intern. Symp. Control. Rel. Bioact. Mater., 17 (1990) 19). In addition, polymers with temperature-sensitive side chains have been developed for temperature-triggered delivery of agrichemicals and drugs (Stewart, R. F., "Temperature Controlled Active Agent Dispenser," U.S. Pat. No. 4,830,855 (1989)).

Polymers that change permeability due to exposure to light have been described (Smets, G. "New Developments in Photochromic Polymers," J. Polym. Sci., Polym. Chem. Ed., 13 (1975) 2223). in addition, delivery systems have been developed that are based on photochemical reactions. Delivery of active agents by photo-induced cleavage of covalent bonds that attaches an active ingredient to a polymer backbone have also been described, although this method of delivery does not rely on a change of coating permeability. In another photochemical-based system, polyamide microspheres were formed from aqueous solutions of diamine (ethylene diamine or hexamethylene diamine) or triamine (diethylenetriamine) and polyvinyl alcohol, which were added to terephthaloyl chloride in benzene/xylenes. Irradiation with UV light caused generation of $N_2$, bursting the microspheres (Mathiowitz, E., M. D. Cohen, and R. Langer, R., "Novel Microcapsules for Delivery Systems," Reactive Polymers, 6 (1987) p. 275).

Systems that rely on magnetic or ultrasound triggers have also been devised (Peppas, N. A. and L. S. Flosenzier, Life Support Syst., 4 (Suppl. 2) (1986) 395.; Langer and Kost, in Pulsed and Self-Regulated Drug Delivery, Kost (ed.), CRC Press, Boca Raton, Fla. (1990) pp. 3–9; Langer, R. S. and J. Kost, U.S. Pat. No. 4,657,543). These triggers increase the rate of diffusion through polymeric matrices.

Systems have also been described for which release of a pharmaceutical is triggered by metabolite concentration, such as insulin release triggered by glucose concentration (Pitt, C. G., Z.-W. Hendren, J. Thompson, and M. C. Wani, "Triggered Drug Delivery Systems," in Advances in Drug Delivery Systems, Anderson and Kim (eds.), Elsevier, Amsterdam (1985) p. 363).

Methods for enzyme-triggered release of pharmaceuticals are also known. These enzyme-triggered systems are based on enzymatic action on a solid substrate. In one system, the active agent is dispersed in pH-sensitive polymer, which erodes at pH 7.4. This is surrounded by enzyme-degradable hydrogel, which is surrounded by a reversibly inactivated enzyme capable of degrading the enzyme-degradable hydrogel. The enzyme is reversibly inactivated by covalent attachment of the hapten (triggering agent) and complexation with antibody against hapten (Heller, J., "Use of Enzymes and Bioerodible Polymers in Self-regulated and Triggered Drug Delivery Systems," in Pulsed and Self-regulated Drug Delivery Systems, J. Kost (ed.), CRC Press, Boca Raton, Fla. (1990) p. 93).

In other systems, enzymes (or the physiological environment) degrade the polymeric membrane itself, leading to release of the active ingredient. In general, enzymatic reaction with solids is very slow, making rapid release impossible (D. L. Wise (Ed.), Biopolymeric Controlled Release Systems, CRC Press, Boca Raton, Fla. (1984)).

Another triggered system consists of a cyclic moiety with an enzyme-sensitive side chain. Cleavage of the side chain leaves a group capable of attacking another carbonyl based side chain to form a cyclic lactone (lactam) and releasing the structure originally bound to the carbonyl side chain (Arnost, Michael J., F. Meneghini, and P. S. Palumbo, Polaroid Corp., "Enzyme Controlled Release System and Organic Conjugate Systems" WPO 88/05827 (i.e. U.S. Pat. No. 5,034,317)). This is a particular type of enzyme-sensitive pro-drug, and no protective membrane is involved.

In another enzymatic triggered system, apple pectin, which is only degraded by colonic flora, is used as a carrier for drugs. Release of indomethacin was enhanced in solutions containing pectolytic bacteria *B. ovatus* and *Klebsiella oxytoca* but not in controls or in solutions containing human *E. coli*, which does not have high pectolytic activity (Rubenstein, A., S. Pathak, M. Friedman, and J. S. Rokem, Proceed. Intern. Syrup. Control. Rel. Bioact. Mater., 17 (1990) 466). This system also does not involve a protective membrane, but rather a carrier matrix.

In yet another system albumin-crosslinked polyvinylpyrrolidone gels were used as enzyme-degradable hydrogels.

Enzymatic degradation of the albumin crosslinks increased the water swelling of the hydrogel (Shalaby, W. S. W., W. E. Blevins and K. Park, "Enzyme-Digestible Properties Associated with Albumin-Crosslinked Hydrogels for Long-Term Oral Drug Delivery," Proceed. Intern. Symp. Control. Rel. Bioact. Mater., 17 (1990) 134).

In another enzymatic triggered system urease-catalyzed conversion of urea raises the pH, which enhances dissolution of methyl vinyl ether-maleic anhydride partial ester copolymer (Heller, J., R. W. Baker, R. M. Gale, R. M., and J. O. Rodin, "Controlled Drug Release by Polymer Dissolution I. Partial Ester of Maleic Anhydride Copolymers," J. Appl. Polym. Sci., 22 (1978) 1991).

In yet another system hydrogels based on acrylic acid, N,N,-dimethylacrylamide and N-tert-butyl-acrylamide, crosslinked with 4,4'-di(methacryloylamino)azobenzene, were synthesized for site-specific delivery of pharmaceuticals to the colon. These hydrogels exhibit low equilibrium swelling at gastric pH. Swelling increases as the gel passes down the GI tract, exposing azo linkages to colonic azoreductases, which cleave the crosslinks, releasing drug dispersed in the gel (Brondsted, H., and J. Kopecek, Proceed. Intern. Symp. Control. Bel. Bioact. Mater., 17(1990)128).

Although the above triggered release devices make a considerable advance in the art there is a continuous search in this art for alternative triggered release devices that allow release over a wide variety of time frames and enable the delivery of a wide variety of active ingredients.

In another field of art, the field of chemical separation, supported-liquid membranes (SLM's) have been used as separation membranes as an alternative to solvent extraction. SLM's comprise a liquid held in the pores of a synthetic membrane (Way, J. D., R. D. Noble, T. M. Flynn, and E. D. Sloan, "Liquid Membrane Transport: A survey," J. Membrane Sci., (1980) 239–259). SLM's prevent mixing of the solutions that they separate. As such they serve to compartmentalize and protect the two solutions involved in the separation. The ability of an SLM to maintain separation between two solutions can vary. This separation maintenance has been extensively studied (H. Takeuchi, K. Takahashi, and W. Goto, "Some Observations on the Stability of Supported Liquid Membranes," J. Membrane, Sci., 34(1987) 19–31; P. R. Danesi, L. Reichley-Yinger, and P. G. Richert, "Lifetime of Supported Liquid Membranes: The Influence of Interfacial Properties, Chemical Composition and Water Transport on the Long-Term Stability of the Membranes," J. Membrane Sci., 31 (1987) 117–145; Takeuchi, H., and M. Nakano, "Progressive Wetting of Supported Liquid Membranes by Aqueous Solutions," J. Membrane Sci., 42 (1989) 183–188; Kim, B.-S. and P. Harriot, "Critical Entry Pressures for Liquids in Hydrophobic Membranes," J. Colloid, Interface Sci., 1115 (1987) 1).

The use of SLM's for a transdermal delivery system has been described (Merkle, H. P., A. Knoch, and G. Gienger, "Release Kinetics of Polymeric Laminates for Transdermal Delivery: Experimental Evaluation and Physical Modeling," In Advances in Drug Delivery Systems, Anderson and Kim (eds.), Elsevier, Amsterdam (1986) p. 99). The device consists of polymeric laminates in which one layer consists of a microporous membrane. The pores of the membrane are filled with a non-polar (i.e. mineral oil, paraffin) media. In these systems release occurs by permeation of the drug through the membrane pore-filling media, providing release of the active ingredient.

PCT Publication WO 92/05775 "Dispensing Device Containing a Hydrophobic Medium" describes a delivery system for the dispensing of an insoluble agent to an aqueous environment. The device comprises a beneficial agent in a hydrophobic medium surrounded by a wall which is in part permeable to the beneficial agent-containing hydrophobic medium. The permeable portion of the wall may be porous with a hydrophobic medium entrained in the pores of the wall.

Although these SLM release devices make a significant advance in the art there is a continuing search for alternative SLM release devices.

SUMMARY OF INVENTION

This invention is directed to supported liquid membrane delivery devices that release a beneficial agent to an aqueous environment following exposure to an environmental trigger. The devices comprise a hydrophilic formulation including a beneficial agent, a microporous hydrophobic support membrane that at least partially surrounds the beneficial agent and a hydrophobic liquid entrained within the pores of the support membrane. The hydrophobic liquid is substantially impermeable to both the aqueous environment and the hydrophilic formulation. The hydrophobic liquid is, however, capable of change such that it becomes substantially permeable to the aqueous environment or hydrophilic formulation.

Another aspect of this invention is a method for the delivery of a beneficial agent to an environment of use which comprises placing the above device into the environment of use.

These devices allow the control of agent release over a wide variety of time frames, allow the delay of agent release for a predetermined time (time lag) and enable the use of a wide variety of materials for their production.

Other objects, features and advantages of the invention will be more apparent to those skilled in the art from the following detailed specification, taken in conjunction with the figures and the accompanying claims.

DETAILED DESCRIPTION OF THE INVENTION

The devices of this invention function as a result of the interaction of an environmental trigger and the hydrophobic liquid. This interaction results in a decrease in the hydrophobicity of the hydrophobic liquid, subsequent transport of an aqueous environmental medium through the porous membrane and subsequent release of beneficial agent. By aqueous medium is meant a composition containing water as the principal liquid component (e.g. physiological fluids, solutions of organic or inorganic substances particularly electrolytes and mixtures of substances in water). The beneficial agent release can occur by simple diffusion, osmotic pumping, or osmotic bursting. The environmental trigger's selection is a convenient starting point in this description because of the interaction between trigger and hydrophobic liquid. Typically, the trigger is selected based on its availability in the environment of use or ease of application. The trigger is desirably present in suitable concentrations, or easily administered to the environment of use such that the dispensing device is activated to achieve the desired release of beneficial agent. The hydrophobic liquid (described below) can be dependent on the particular trigger selected.

Any trigger (trigger means) may be used that activates the dispensing devices of this invention to release the beneficial agent. Exemplary triggers include mammalian enzymes, plant enzymes, fungal enzymes, bacteria or viral enzymes, nucleophiles, reducing agents, oxidizing agents, heat (e.g. 35° C. to 45° C.) and light (e.g. 300 nm to 340 nm). A more detailed list of triggers is given below (Table 1) in a listing that provides a preferred coordination listing of triggers and hydrophobic liquids.

Any hydrophobic liquid (hydrophobic liquid means) may be used that inhibits release of the beneficial agent and is responsive to the environmental trigger. The hydrophobic liquid should be capable of transformation such that it becomes permeable to the aqueous environment or the beneficial agent containing hydrophilic formulation. The interaction between the support membrane, hydrophobic liquid, and aqueous solution should change in response to the trigger, to allow aqueous flux through the pores of the membrane. This transformation can be a result of a variety of changes in the hydrophobic liquid. The hydrophobic liquid may form a hydrophilic moiety preferably a carboxylic acid, amine, thiol, alcohol, sulfonic acid or phosphoric acid. Thus, preferably the hydrophobic liquid undergoes hydrolysis or reduction to form the above hydrophilic moieties. The transformation increases the hydrophilicity of the liquid thus increasing the permeability of water by lowering the interfacial tension between the support membrane and water or the liquid and water. This allows the beneficial agent to be released, either by diffusion or by some other mechanism initiated by entering water (such as osmotic bursting).

The hydrophobic liquid may have a single component, be a solution of several components in an inert solvent, or be a suspension. By inert is meant the solvent does not react with the trigger or the aqueous environment. It is intended that devices where components are individually solids (but under the conditions of use that the total mixture is substantially liquid) are within the scope of this invention.

Preferably the hydrophobic liquid has a solubility of less than 15 wt % in water. This inhibits the liquid from diffusing into the aqueous environment prior to being triggered. However, the limiting solubility can vary depending on the membrane thickness, support membrane average pore size and pore size distribution, time lag prior to triggering the device, and viscosity. Preferably the hydrophobic liquid forms a contact angle of less than 90° with the microporous hydrophobic support membrane material (described below) as this facilitates wetting the support membrane. Preferably the hydrophobic liquid has a viscosity of less than about $10^6$ centipoise (cp) as this facilitates relatively fast reaction times compared with solids. Preferably the hydrophobic liquid has a permeability to water of less than $9\times10^{-6}$ cc STP -cm/cm$^2$ -sec -cmHg as this facilitates the liquid acting as a barrier to water prior to encountering the trigger. However, the limiting permeability to water is also dependent upon membrane thickness, support membrane average pore size and pore size distribution and the time lag desired between exposure to the trigger and activation (i.e. agent release). Preferably this permeability to water changes substantially (i.e. at least an order of magnitude) after the device is activated. Preferably the hydrophobic liquid is compatible with the support membrane (e.g. the liquid does not dissolve, weaken, or be absorbed by the support membrane). In addition, low-volatility liquids (e.g. 10 cm of Hg at 25° C.) are desirable for normal storage/shelf life; however, if outer barrier coatings are used or if the devices are used shortly after the pores are loaded, liquids having high volatility can be used.

Exemplary hydrophobic materials that are liquids (or with appropriate solvents are liquids) include triglycerides, fatty anhydrides, fatty acid esters of cholesterol, fatty acid peroxides, long chain esters, hydrophobic amino acid esters, hydrophobic dipeptide derivatives, hydrophobic polyesters, or hydrophobic disulfides. More preferably the triglycerides are compounds having the general formula $CH_3(CH_2)_aCOOCH_2CH_2(OOC(CH_2)_bCH_3)CH_2OCO(CH_2)_cCH_3$ where a, b and c are from 4 to 24. Preferred fatty anhydrides include compounds of the formula $CH_3(CH_2)_dCOOCO(CH_2)_eCH_3$ where d and e are from 6 to 24. Preferred fatty acid esters of cholesterol include a compound of the formula $(C_{27}H_{46})$—O—C(O)—R, where R is $CH_3(CH_2)_q$, and q is 0–20. Preferred fatty acid peroxides include compounds of the formula $(CH_3(CH_2)_fCOO)_2$ where f is independently 6 to 24. Preferred long chain esters include compounds of the formula $CH_3(CH_2)_gCOO(CH_2)_hCH_3$ where g and h are independently from 2 to 24. Preferred hydrophobic amino acid esters include N-protected amino acid esters of the structure X—CO—NHCH(Z)COO—Y, where X and Y are independently alkyl ($C_6$–$C_{20}$), branched alkyl ($C_6$–$C_{20}$), or aralkyl ($C_6$–$C_{20}$), and Z is one of the following: (resultant amino acid is given in parentheses): phenyl methyl (phenylalanine), (2-methyl)propyl (leucine), 2-butyl (isoleucine), p-hydroxy-phenylmethyl (tryosine), indolylmethyl (tryptophan), 2-propyl (valine), (2-methylthio)ethyl (methionine), 2-carboxyl-ethyl (glutamic acid), carboxymethyl (aspartic acid), carboxamidomethyl (asparagine), hydroxymethyl (serine), (1-hydroxy)ethyl (threonine), or hydrogen (glycine). All amino acids are of the L configuration.

Preferred hydrophobic dipeptides include protected dipeptides of the structure X—CO—NHCH(W)CO—NHCH(V)COO—Y or X—CO—NHCH(W)CO—NHCH(V)CO—NHCH—Y, where X and Y are independently alkyl ($C_6$–$C_{20}$), branched alkyl ($C_6$–$C_{20}$), or aralkyl ($C_6$–$C_{20}$), and W and V are both or separately one of the following: (resultant amino acid is given in parentheses): phenyl methyl (phenylalanine), (2-methyl)propyl (leucine), 2-butyl (isoleucine), p-hydroxy-phenylmethyl (tyrosine), indolylmethyl (tryptophan), 2-propyl (valine), (2-methylthio)ethyl (methionine), 2-carboxy-ethyl (glutamic acid), carboxymethyl (aspartic acid), carboxamidomethyl (asparagine), hydroxymethyl (serine), (1-hydroxy)ethyl (threonine), or hydrogen (glycine). All amino acids are of the L configuration.

Especially preferred triglycerides include triolain, tricaprylin, trilaurin, olive oil, palm oil, rapeseed oil, coconut oil, cocoa butter, sesame seed oil, corn oil, linseed oil, cottonseed oil, peanut oil, safflower oil, soybean oil, and sunflower oil.

Especially preferred fatty anhydrides include caprylic anhydride, lauric anhydride, myristic anhydride, and stearic anhydride. Especially preferred fatty acid esters of cholesterol include cholesterol butyrate, cholesterol laureate, cholesterol caprylate, cholesterol stearate and cholesterol oleate. Especially preferred fatty acid peroxides include dilauryl peroxide and dicapryl peroxide. Especially preferred long chain esters include ethyl caprylate, ethyl laureate, ethyl oleate, ethyl stearate, butyl caprylate, butyl laureate, butyl oleate, butyl stearate, octyl caprylate, and octyl oleate.

An especially preferred polyester and hydrophobic disulfide are poly (1,8-dihydroxy-octyl adipate) and dioctyl disulfide, respectively.

As described above, the devices of this invention have a trigger-hydrophobic liquid interaction. The above descriptions of triggers and hydrophobic liquids provide sufficient information such that one skilled in the art can select appropriate combinations of triggers and hydrophobic liquids for the desired use. The following Table I provides a preferred list of triggers referred to earlier. In addition, the following Table I provides an especially preferred list of trigger-hydrophobic liquid combinations.

Table I includes "Enzyme Commission" numbers (EC) numbers which correspond to the class of enzymes to which the particular enzyme belongs.

TABLE I

| TRIGGERS | HYDROPHOBIC LIQUID |
| --- | --- |
| MAMMALIAN ENZYMES | |
| Pancreatic lipase (EC 3.1.1.3) | Triglycerides, fatty anhydrides |
| Gastric lipase | Triglycerides, fatty anhydrides |
| Lingual lipase | Triglycerides, fatty anhydrides |
| Lipoprotein lipase | Triglycerides, fatty anhydrides |
| Hepatic endothelial lipase | Triglycerides, fatty anhydrides |
| Lysosomal acid lipase | Triglycerides, fatty anhydrides |
| Adipose tissue lipase | Triglycerides, fatty anhydrides |
| Cholesterol esterase | Fatty acid ester of cholesterol |
| Liver esterase (EC 3.1.1.1) | Long chain esters |
| Cystolic and other esterases | Long chain esters |
| Amino acylase | Fatty-acid derivatives of amino acid esters |
| Azo-reductase | Hydrophobic azo-compounds |
| Serine Proteases including: | |
| chymotrypsin (EC 3.4.21.1) | Hydrophobic esters of amino acid derivatives |
| trypsin (EC 3.4.21.4) | Hydrophobic esters of amino acid derivatives |
| elastase (EC 3.4.21.36) | Hydrophobic esters of amino acid derivatives |
| kallikrein (EC 3.4.21.35) | Hydrophobic esters of amino acid derivatives |
| carboxypeptidase | Hydrophobic esters of amino acid derivatives |
| Endoproteinase Arg—C (EC 3.4.21.40) | Hydrophobic esters of amino acid derivatives |
| Factor $X_A$ (EC 3.4.21.6) | Hydrophobic esters of amino acid derivatives |
| Thrombin (EC 3.4.4.13) | Hydrophobic esters of amino acid derivatives |
| plasmin (EC 3.4.21.7) | Hydrophobic esters of amino acid derivatives |
| Cysteine proteases including: | |
| cathepsin B (EC 3.4.22.1) | Hydrophobic esters of amino acid derivatives |
| cathepsin C (EC 3.4.14.1) | Hydrophobic esters of amino acid derivatives |
| cathepsin D (EC 3.4.23.5) | Hydrophobic esters of amino acid derivatives |
| cathepsin G (EC 3.4.21.20) | Hydrophobic esters of amino acid derivatives |
| cathepsin H | Hydrophobic esters of amino acid derivatives |
| cathepsin L | Hydrophobic esters of amino acid derivatives |
| Aspartyl proteases including: | |
| Pepsin (EC 3.4.23.1) | Hydrophobic dipeptides |
| Rennin | Hydrophobic dipeptides |
| PLANT ENZYMES | |
| Oil seed lipases | Triglycerides, fatty anhydrides |

TABLE I-continued

| TRIGGERS | HYDROPHOBIC LIQUID |
| --- | --- |
| Glyoxysomal lipases | Triglycerides, fatty anhydrides |
| Cereal grain lipases | Triglycerides, fatty anhydrides |
| Lipid acyl hydrolase | Triglycerides, fatty anhydrides |
| Cysteine proteases including: | |
| papain (EC 3.4.22.2) | Hydrophobic esters of amino acid derivatives |
| bromelain (EC 3.4.22.4) | Hydrophobic esters of amino acid derivatives |
| ficin (EC 3.4.22.3) | Hydrophobic esters of amino acid derivatives |
| chymopapain (EC 3.4.22.6) | Hydrophobic esters of amino acid derivatives |
| papaya protease III | Hydrophobic esters of amino acid derivatives |
| papaya protease IV | Hydrophobic esters of amino acid derivatives |
| FUNGAL ENZYMES | |
| Fungal lipases | Triglycerides, fatty anhydrides |
| Fungal proteases | Hydrophobic esters of amino acids |
| Fungal esterases | Triglycerides, fatty anhydrides, esters |
| Fungal cutinases | Polyesters |
| BACTERIAL OR VIRAL ENZYMES | |
| Bacterial lipases | Triglycerides, fatty anhydrides |
| Bacterial esterases | Hydrophobic esters |
| Serine proteases including: | |
| subtilisin (subtilopeptidase A) (EC 3.4.21.14) | Hydrophobic esters of amino acid derivatives |
| proteinase K (EC 3.4.21.14) | Hydrophobic esters of amino acid derivatives |
| protease V8 (EC 3.4.21.9) | Hydrophobic esters of amino acid derivatives |
| Endoprotease Lys—C (EC 3.4.99.30) | Hydrophobic esters of amino acid derivatives |
| Ancrod (EC 3.4.21.28) | Hydrophobic esters of amino acid derivatives |
| Cysteine proteases including: | |
| clostripain (EC 3.4.22.8) | Hydrophobic esters of amino acid derivatives |
| Metallo-proteases including: | |
| Thermolysin (EC 3.4.24.4) | Hydrophobic dipeptides |
| Dispase (EC 3.4.24.4) | Hydrophobic dipeptides |
| Aspartyl Proteases including: | |
| HIV protease | Hydrophobic dipeptides |
| CHEMICAL TRIGGERS | |
| Nucleophiles | |
| ammonia | Fatty acid anhydrides |
| hydrazine | Fatty acid anhydrides |
| substituted hydrazines | Fatty acid anhydrides |
| hydroxylamine | Fatty acid anhydrides |
| Reducing agents | |
| Borohydride salts | Fatty diacyl peroxides |
| Thiols | Hydrophobic disulfides |
| PHYSICAL TRIGGERS | |
| Heat | high melting triglyceride with suspended lipase |
| Light | Fatty acid esters of bis (o-nitrophenyl)methanol |

The hydrophobic liquid may be entrained alone in the membrane or may be mixed with other components such as inert solvents. Such inert solvents are defined as being unreactive with the trigger or the aqueous environment. By combining the hydrophobic liquid with an inert solvent, the time lag prior to delivery of the beneficial agent may be tailored. Thus, preferably a mixture of hydrophobic liquid and inert solvent is used sufficient to provide the desired time lag (e.g. sufficient to provide release to the duodenum, jejunum, colon, or ileum). Preferred solvents include: hydrocarbons such as squalane, squalene, tetradecane, hexadecane, paraffin oil and light and heavy mineral oil; carboxylic acid esters such as ethyl caprylate, propyl caprylate, butyl caprylate, ethyl laureate, propyl laureate, butyl laurate, ethyl caproate, propyl caproate, and butyl caproate; ethers such as butyl ether, hexyl ether, octyl ether, propyl butyl ether, and pentyl ether; ketones such as dibutyl ketones, dipentyl ketone, dihexyl ketone, dioctyl ketone, 2-octanone, 3-octanone, 4-octanone, 2-decanone, 3-decanone, 4-decanone, 5-decanone, 2-undecanone, 3-undecanone, 4-undecanone, and 5-undecanone; and sulfate diesters such as dioctylsulfate.

The hydrophobic liquid may also contain suspended solids which become activated by the trigger (e.g. a lipase suspended in semisolid cocoa butter). Here the enzyme is inactive against the solid substrate until the trigger, heat, is applied, melting the butter and causing the suspended lipase to become active. Typically the solvent/hydrophobic liquid is used in a weight proportion of 0/100 to 99/1.

Any microporous hydrophobic support membrane (membrane means) that provides structural support for the devices of this invention, is solid under the conditions of use and entrains the hydrophobic liquid may be used in this invention. Although, typically the support membrane totally surrounds the beneficial agent, the support membrane may be combined with an impermeable wall portion to totally surround the beneficial agent if desired. Preferably the support membrane is polymeric or waxes although appropriately treated inorganic materials such as ceramics, metals or glasses may be used. Preferably the support membrane is wetted by the hydrophobic liquid rather than by the surrounding aqueous medium. Preferably the contact angle of the water with the membrane is greater than 50°. Preferably, since the membrane functions as a water barrier the membrane permeability to water is less than $9 \times 10^{-6}$cc STP-cm/$cm^2$-sec-cmHg. Preferably the membrane material (in the nonporous state) is substantially impermeable to the beneficial agent or beneficial agent-containing formulation. By impermeable is meant less than 5% of the agent or formulation is lost over a 48 hour period. Although the membrane thickness may be any dimension that provides the structural stability and hydrophobicity desired, the membrane is preferably 1 µm to 1 mm in thickness. Preferably the membrane is 10 µm to 300 µm for human health applications. Preferably there is a total pore volume of less than 95% and a maximum pore size of less than 100 µm in diameter. The microporous membrane has at least one continuous pathway through the membrane thickness.

The following is a preferred listing of polymeric support membranes. The polymer's molecular weight should be of such a size that the polymer is solid at the temperature of use and appropriate for the application (e.g., pharmaceutically acceptable or EPA approved).

Cellulose esters.

Polycarbonates such as Bispheonol A poly (carbonates).

Polyalkenes such as poly(ethylene), poly(propylene), poly(vinylidene fluoride), poly(tetrafluoroethylene), poly(1, 2-dimethyl-1-butenylene), poly(1-bromo-1-butenylene), poly(1,butene), poly(1-chloro-1-butenylene), poly(1-decyl-1-butenylene), poly(1-hexene), poly(1-isopropyl-1-butenylene), poly(1-pentene), poly(3-vinylpyrene), poly(4-methoxy-1-butenylene); poly(ethylene-co-methyl styrene), poly vinyl-chloride, poly(ethylene-co-tetrafluoroethylene), poly(ethylene-terephthalate), poly(dodecafluorobutoxylethylene), poly(hexafluoroprolylene), poly(hexyloxyethylene), poly(isobutene), poly(isobutene-co-isoprene), poly(isoprene), poly-butadiene, poly[(pentafluoroethyl)ethylene], poly[2-ethylhexyloxy)ethylene], poly(butylethylene), poly(tertbutylethylene), poly(cylclohexylethylene), poly[(cyclohexylmethyl)ethylene], poly(cyclopentylethylene), poly(decylethylene), poly(dichloroethylene), poly(difluoroethylene), poly(dodecylethylene), poly(neopentylethylene) and poly(propylethylene).

Polystyrenes such as poly(2,4-dimethyl styrene), poly(2-methyl styrene), poly(3-methyl styrene), poly(4-methoxystyrene), poly(4-methoxystyrene-stat-styrene), poly(4-methyl styrene), poly(isopentyl styrene) and poly(isopropyl styrene).

Polyvinyl esters or poly-vinyl ethers such as poly(benzoylethylene), poly(butoxyethylene), poly(chloroprene), poly(cyclohexloxyethylene), poly(decyloxyethylene) and poly(vinyl acetate)poly(vinyltrimethylstyrene)

Polysiloxanes such as poly(dimethylsiloxane) and poly(dimethylsiloxane).

Polyacrylates such as poly(acrylic acid) higher alkyl esters, poly(ethyl methacrylate), poly(hexadecyl methacrylate-co-methyl methacrylate), poly(methyl acrylate-co-styrene), poly(n-butyl methacrylate), poly(n-butyl-acrylate), poly(cyclododecyl acrylate), poly(benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate) and poly(octyl methacrylate).

Polyamides such as poly(iminoadipoyliminododecamethylene) and poly(iminoadipoyliminohexamethylene).

Polyethers such as poly(octyloxyethylene), poly(oxyphenylethylene), poly(oxypropylene), poly(pentyloxyethylene), poly(phenoxy styrene), poly(secbutroxylethylene) and poly(tert-butoxyethylene).

Exemplary membrane waxes include: insect and animal waxes such as chinese insect wax, beeswax, spermaceti, fats and wool wax; vegetable waxes such as bamboo leaf wax, candelilla wax, carnauba wax, Japan wax, ouricury wax, Jojoba wax, bayberry wax, Douglas-Fir wax, cotton wax, cranberry wax, cape berry wax, rice-bran wax, castor wax, indian corn wax, hydrogenated vegetable oils (e.g., castor, palm, cottonseed, soybean), sorghum grain wax, Spanish moss wax, sugarcane wax, caranda wax, bleached wax, Esparto wax, flax wax, Madagascar wax, orange peel wax, shellac wax, sisal hemp wax and rice wax; mineral waxes such as Montan wax, peat waxes, petroleum wax, petroleum ceresin, ozokerite wax, microcrystalline wax and paraffins; and synthetic waxes such as polyethylene wax, Fischer-Tropsch wax, chemically modified hydrocarbon waxes and cetyl esters wax.

Preferably the membrane (having the hydrophobic liquid entrained therein) is impermeable to the beneficial agent or beneficial agent containing hydrophilic formulation. By impermeable is meant that in the environment of use less than 20% of the total beneficial agent is released by diffusion through the support membrane prior to triggering. It is especially preferred that less than 5% of the total beneficial agent is released by diffusion through the support membrane prior to triggering.

The beneficial agents used in the devices of this invention include for example any physiologically or pharmacologically active substance that produces a localized or systemic effect in animals including mammals (e.g. human beings).

Examples of active substances include inorganic and organic compounds such as drugs that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autacoid systems, alimentary and excretory systems, inhibitors of autocoids and histamine systems. The pharmaceutical agent that can be delivered for acting on these systems includes antidepressants, hypnotics, sedatives, psychic energizers, tranquilizers, anti-convulsants, muscle relaxants, antisecretories, anti-parkinson agents, analgesics, anti-inflammatory agents, local anesthetics, muscle contractants, antibiotics, anti-microbials, anthelmintics, anti-malarials, hormonal agents, contraceptives, histamines, antihistamines, adrenergic agents, diuretics, antiscabiosis, anti-pediculars, anti-parasitics, anti-neoplastic agents, hypoglycemics, electrolytes, vitamins, diagnostic agents and cardiovascular pharmaceuticals.

Also included in such active substances are prodrugs of the above-described drugs. Such drugs or prodrugs can be in a variety of forms such as the pharmaceutically acceptable salts thereof.

The term beneficial agent is also meant to include other substances for which it is desirable and/or advantageous to control delivery into an environment of use. Examples of such substances include pesticides, fertilizers, algacides, insect growth regulators, pheromones, reaction catalysts and enzymes.

Preferably the beneficial agents are hydrophilic, or are contained in a hydrophilic formulation. By hydrophilic is meant that it will not diffuse through, or, not have high solubility in either the hydrophobic support membrane or the hydrophobic liquid. Alternatively by hydrophilic is meant that the formulation has no more than a certain flux through the hydrophobic liquid containing membrane. Using, as an example, 20% released in 3 hours from a tablet with a 100 mg drug load and a 3 cm$^2$ surface area, a maximum flux of beneficial agent/hydrophilic formulation is 0.05 mg.cm/cm$^2$ hr. This inhibits premature leaking of the beneficial agent through the hydrophobic membrane into the environment of use. Materials in addition to the beneficial agent that may be included in the hydrophilic formulations include viscosity modifiers, antioxidants, stabilizers, pH controlling agents, flavoring agents, binding agents, tablet disintegrants, osmotic agents, swellable components (e.g. hydrogel), lubricants, glidants, adsorbents and inert diluents etc. Typical examples are: binding agents such as carboxymethyl cellulose, hydroxyethyl cellulose, acacia gum, guar gum, microcrystalline cellulose, starch sodium alginate, polyethylene glycols, corn syrup, sucrose, lactose, mannitol, calcium phosphate, and ethyl cellulose; tablet disintegrants such as starch, microcrystalline cellulose, clays, and sodium alginate; lubricants such as talc, polyethylene glycols, corn starch, sodium benzoate, and sodium acetate; glidants such as microfine silicas, corn starch, microcrystalline cellulose and talc; adsorbents such as silicas, and starches; inert diluents such as lactose, dextrose, starch, microcrystalline cellulose, calcium phosphate, calcium sulfate, sucrose, mannitol, kaolin, and magnesium aluminum sulfate; and osmotic agents and buffering agents such as citric acid, sodium phosphate, glucose, potassium citrate, potassium sorbate, sodium bicarbonate, sodium chloride, and sodium citrate; and water expanding compounds such as esters of hyaluronic acid, esters of alginic acid, carboxymethylcellulose, guar, modified cellulose gum, sodium starch glycolate, propylene glycol ester of alginic acid, xanthan gum, acrylic acid grafted starch and hydrolyzed acrylamide.

The devices of this invention can be advantageously tailored by altering the time lag between exposure of the device to the trigger (e.g. enzyme) and release of the beneficial agent. Thus, preferably the membrane pores and membrane thickness are of a number and size sufficient to provide the desired time lag (e.g., sufficient time lag to provide release to the ileum, colon or duodenum). Typically, support membranes with more or larger pores become permeable to water faster than similar membranes with smaller pores (e.g., see Examples 44, 45, 46 and 48). In addition, thinner membranes typically open faster than thicker membranes (e.g. see Examples 51–53).

Alternatively, the time lag can be tailored by changing the composition of the hydrophobic liquid. Thus, preferably the hydrophobic liquid has a composition such that it provides the desired time lag (e.g., sufficient time lag to provide release to the ileum, colon or duodenum).

In addition, the release profile can be tailored so that the release duration is from instantaneous (i.e. bursting) to 24 hours and more. For example, a tablet containing a core formulation with a water-swellable hydrogel designed to expand and burst the tablet would have a very shod release duration, essentially as fast as the beneficial agent could dissolve. A tablet where the beneficial agent is released by osmotic pumping or diffusion through the pores would have a longer release duration.

Although any mixture of the above ingredients may be used that satisfactorily delivers the beneficial agent, typically the hydrophobic liquid is 0.01 to 30% by weight of the device and the membrane (including hydrophobic liquid) is typically 1 to 30% of the device. Preferably the hydrophobic liquid is 0.01% to 20% of the device and the membrane (including hydrophobic liquid) is 1 to 20% of the device. The amount of beneficial agent is the amount that is sufficient to achieve the desired effect (e.g. therapeutic effect). The remainder weight is made up of any desired hydrophilic formulation ingredients (described above) and other additives.

The devices of this invention can also be administered within a capsule comprising a water soluble wall. For example, the devices can be manufactured to be of suitable size for inclusion either singularly or multiply within a gelatin capsule such that when the capsule dissolves the device(s) are released into the environment of use. While the devices to be included within a capsule can be of a variety of shapes, a preferred shape for such devices is spherical or substantially spherical. The exact number and size of such devices can and will be determined according to a variety of well known factors. For example, the environment of use, the beneficial agent or agents, the amount of beneficial agent and the rate of release are all factors to be considered in determining the size, shape, and number of devices to be included in such capsules as well as the composition of the capsule.

The dispensing device shape and dimensions can vary based on the particular application (e.g. tablet). Common exemplary shapes are spherical cylindrical, tablet-shape, and capsular-shape. The dispensing device dimensions may vary with the desired application (e.g. cattle tablets, human tablets). The shape and size may also vary depending on the application so that for example the tablet is suitable depending on the quantity and rate of beneficial agent delivery which vary based on the application, However, typical capsule dimensions range from about 0.4 inch to about 1 inch in length and about 0.1 inch to about 0.4 inch in diameter for human health applications. For animal applications such as ruminal delivery to cattle typical dimensions range from about 2 inches to about 4 inches in length and about 0.5 inch to about 1.2 inches in diameter.

Preferred exemplary devices include a polyvinylidenefluoride or polyalkene porous membrane with a triglyceride entrained therein. Preferred within this group are devices where the hydrophobic liquid is triolein, olive oil or tricaprylin in squalane in concentrations of 20 to 100 wt %. Other preferred devices include polyvinylidenefluoride or polyalkene porous membranes where the hydrophobic liquid is a solution of octanoyl-L-phenylalanine octyl ester 20 wt % in ethyl caprylate or ethyl caprylate alone. Preferably the above membranes are in the form of a tablet, bead or capsule surrounding a core formulation of the beneficial agent and a component that swells in the presence of water (e.g., hydrogel).

Another preferred device comprises a polyvinylidenefluoride porous membrane with a solution of a hydrophobic ester of an N-protected amino acid, selected to be a substrate for a targeted protease. For example, a mixture of N-tert-butyloxycarbonyl-L-phenylalanine 1-octyl ester, N-tert-butyl-oxycarbonyl-L-phenylalanine 2-octyl ester and N-tert-butyl-oxycarbonyl-L-phenylalanine 3-octyl ester (the mixture remains a liquid at room temperature) can be used. This device is particularly useful in environments containing the protease chymotrypsin, or similar enzymes.

Figure 1:
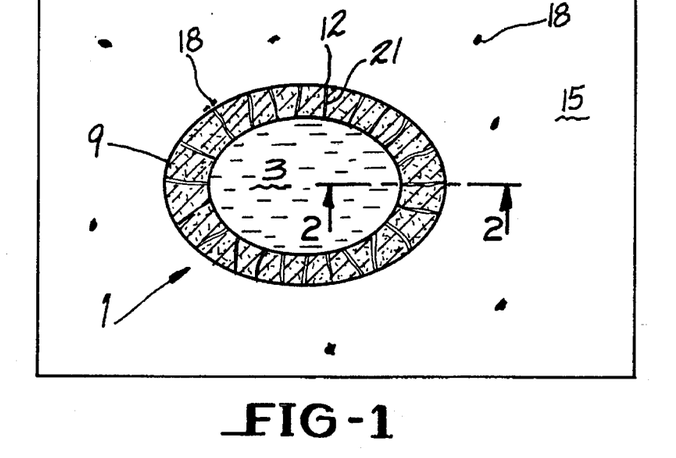
FIG. 1 is a cross-sectional view of an exemplary device of this invention.
Figure 2:
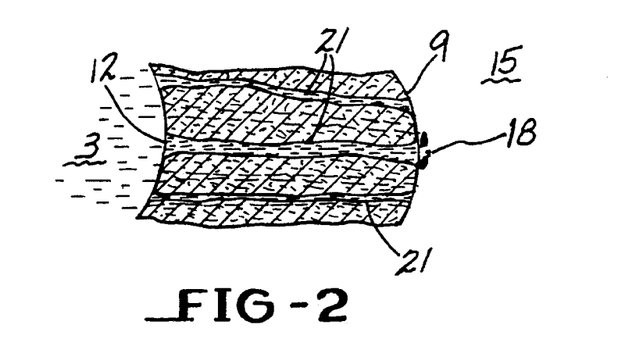
FIG. 2 is a sectional view taken along line 2—2 of FIG. 1 showing the support membrane in greater detail.

A clearer understanding of the devices of this invention may be had by reference to FIGS. 1 and 2. The beneficial agent and other excipients are contained in the core 3 surrounded by the porous support membrane 9. Entrained in the pores 21 (e.g. by capillarity) of the support membrane 9 is the hydrophobic liquid 12. External to the device 1 is the environment of use 15 including the trigger 18.

The devices of this invention having the above described desired characteristics may be made using the above described materials using the following processes and other conventional methods.

For example, capsules may be produced by forming a cap and body of sintered polymers. Typically the desired polymers are molded into the desired porous shapes and sintered. A solution of the desired hydrophobic liquid is imbibed into the porous sintered structure by differential pressure application. The beneficial agent, and any other ingredients are placed into the structure as a mixture or in succession. Then the capsule is assembled and if desired joined by conventional methods used for gelatin capsules. Preferably water insoluble joining methods are used because, if the capsule comes apart, it may not function in the desired manner. For ruminal applications, an impermeable wall portion may be joined between the cap and body portions.

In addition, microporous films can be sealed together covering the beneficial agents to form pouches. The pores of the films can be filled with the hydrophobic liquid by immersion in such liquid. The liquid will fill the pores by capillary action. Alternatively microporous fibers can have their ends sealed enclosing the active agents followed by immersion in the desired hydrophobic liquid.

Tablets may be made for example by compressing blends (using conventional tabletting methods) of the beneficial agent and any other additives to form a tablet core.

Granules of the desired beneficial agent and other additives may be made by extrusion-spheronization or fluid-bed granulation.

The above described granules, tablets and other multiparticulates and capsules may be coated with the porous membranes described above to prepare the devices of this invention. Microporous coatings can be made by a variety of methods, such as phase inversion, scintering, leaching, and irradiation. Several different phase-inversion methods, such as the vapor quench process, the dry process, the liquid quench process, and the thermal process, can be used to form microporous coatings.

In the vapor quench process, membrane formation is accomplished by penetration of a precipitant for the polymer into the solution film from the vapor phase, which may be saturated with the solvent used. A porous membrane is produced without a skin and with an even distribution of pores over the membrane thickness.

In the dry process, the polymer is dissolved in a mixture of a solvent and a poor solvent, of which the solvent is more volatile. The polymer precipitates when the mixture shifts in composition during evaporation to a higher nonsolvent content. A skinned or nonskinned microporous membrane can be the result.

In the liquid quench process, film formation is caused by the immersion of the cast polymer film in a nonsolvent bath. The polymer precipitates as a result of solvent loss and nonsolvent penetration (exchange of the solvent with nonsolvent). A skinned or nonskinned membrane can be the result.

In the thermal process, a solution of polymer in a mixed solvent, which is on the verge of precipitation, is brought to phase separation by a cooling step. When evaporation of the solvent has not been prevented, the membrane can have a skin. Microporous coatings can also be made by inclusion of a leachable component in the coating formulation. For example, small sugar, salt, or water-soluble polymer particles could be suspended or dissolved in the coating solution. Once the coating is applied, then the water-soluble materials can be leached out by immersion in water, forming a microporous structure.

Microporous hydrophobic films have also been made by scintering particles of hydrophobic polymers or ceramics or metals together under heat and pressure. Microporous hydrophobic films are also commonly made by irradiation. Films can be cured (precipitated) by irradiation, forming a microporous structure. In addition, pores can be formed in dense films by a nucleation track-etched method. All of these methods for forming hydrophobic microporous films have been described in the literature, especially for use as membranes for separations (*Synthetic Polymer Membranes,* by R. E. Kesting, John Wiley & Sons, 1985).

To fill the pores of the support membrane with a hydrophobic liquid, the membrane can simply be immersed in the hydrophobic liquid. To increase the rate at which the liquid fills the pores and/or to ensure that all the pores become filled, the immersed matrix or coating may be subjected to a vacuum or pressurization.

The hydrophobic liquid can also be incorporated into the microporous coatings as the coatings are being applied. The hydrophobic liquid can serve as the pore-former in phase-inversion processes or serve as the "leachable" component. The technique of including the hydrophobic liquid into the coating solution has been demonstrated in the production of polyethylene/olive oil capsules made by a thermal phase-inversion process (described in Example 66, although the olive oil used to produce the microporous capsules was replaced with fresh olive oil for direct comparison with the olive oil-loaded Kynar capsules (Pennwalt Corp., Philadelphia, Pa.)). It is envisioned that this type of coating process (with the hydrophobic liquid included in the microporous coating formulation) will be particularly useful for coating multiparticulates since the coating solution is similar to melt coatings currently applied to multiparticulates. In addition, incorporating the hydrophobic liquid into the coating solution eliminates additional processing steps to load the pores of the coating with the hydrophobic liquid.

These triggered-release coatings can be applied using conventional coating equipment. Microporous coatings have been applied using a fluid-bed coater, a pan-coater, a spray-drier, and by a dip-coating process (similar to the process used to make gelatin capsules). Thus, triggered-release coatings can be applied to tablets, multiparticulates, capsules, or formed into different geometries such as capsules (same as currently available gelatin capsules).

Methods for using the devices of this invention include administration of the appropriate devices to animals via oral administration or by insertion of the appropriate devices into a body cavity of the animal. Devices of this invention can also be used to deliver agents to such environments of use as swimming pools, ponds, fish tanks, soil, crops and aqueous chemical and/or enzymatic reaction systems. In such cases, the devices are placed into the desired environment of use. The devices of this invention require that such environment of use be either aqueous or provide for contact of the device with water or other aqueous medium.

A key advantage of the devices of this invention is that the release rate of the beneficial agent can be tailored in a variety of fashions. Both the duration of the release and the time between being triggered and release may be tailored to achieve the desired release profile. Because the trigger is interacting with a liquid rather than a solid, faster response is possible, but slow responses may be achieved by manipulating the nature of the hydrophobic liquid. Further, the devices of this invention allow the use of a wide variety of materials in order to accommodate a wide variety of use environments. Thus, devices having membranes sensitive to a wide variety of triggers can be constructed by changing the hydrophobic liquid. Since the hydrophobic liquid is not used for structural support or integrity of the membrane, a wide variety of hydrophobic liquids can be used. Finally, the devices are simple to construct. The beneficial-agent-containing core can be made from a variety of materials and the core is simply surrounded by a rate-controlling membrane according to this invention.

It should be understood that the invention is not limited to the particular embodiments shown and described herein, but that various changes and modifications may be made without departing from the spirit and scope of this novel concept as defined by the following claims.

EXAMPLE 1

Water Permeability Triggered by Pancreatic Lipase

A supported-liquid membrane was produced by filling the pores of a disk of Accurel A3 polypropylene membrane (the support membrane) (Enka America, Ashville, N.C.) with olive oil (purified grade, Sigma Chemical Co., St. Louis, Mo.)). The membrane had a thickness of 150 μm and an effective pore size of 0.2 μm. The disk was blotted to remove excess oil, and fitted in a weight-gain device (FIG. 2). The weight-gain device 31 was filled with 0.75 g of Waterlock J-500, water sequestering material (Grain Processing Corp., Muscatine, Iowa) 33. The device was placed in a receptor solution 6 consisting of 0.125M phosphate buffer, pH 7.5, 0.2 wt % bile salt extract (Sigma Chemical Co., St. Louis, Mo.), and 5 mg/ml porcine pancreatic lipase (PPL, Sigma) such that the membrane 39 was in contact with the solution. As water 6 permeated the membrane 39, it was trapped by the sequesterant 33, increasing the weight of the entire device. Water flux through the membrane was calculated from the best linear portion of the weight gain per time plot. Time lag is defined as the extrapolation of this linear portion back to the X-axis, and is a measure of the time between the first exposure to the enzyme and the onset of water flux through the membrane.

Once exposed to the enzyme trigger, there was a time lag of 1 hour before water flux was detected. After this time, the measured water flux, normalized for membrane area, was 500 mg/cm$^2$/hr. In a control experiment in which the receptor solution lacked enzyme, the water flux was essentially zero (0.75 mg/cm$^2$/hr) for the 12-hour duration of the test.

Example 1 demonstrates that the membrane substantially prevents water transport in the absence of the enzyme, but when the enzyme is present, water transport is significant. The enzyme triggers the change in permeability. In the following examples, various combinations of triggering agent, support membrane, and hydrophobic liquid are examined. In all examples, a water-flux test is always performed in the absence of the triggering agent, and is listed as "control".

EXAMPLES 2 TO 14

Water Flux Can be Altered by Changing Concentration of Hydrophobic Liquid (Olive Oil)

Example 1 is repeated, except that the hydrophobic liquid consisted of varying concentrations of olive oil in squalane, an inert hydrocarbon solvent. Profound changes in water flux were achieved with small changes in olive oil. These results are presented in Table 2. In all cases, the water flux in the presence of PPL was much greater than that for the controls (receptor solution without PPL.)

TABLE 2

The Effect of Olive Oil on Water Flux and Time Lag

| Ex No. | % Olive Oil in Squalane | Water Flux (mg/cm$^2$/hr) | Control (mg/cm$^2$/hr) | Time Lag (hrs) | N* |
|---|---|---|---|---|---|
| 2 | 1 | 1.6 ± 1.4 | 0.4 | 0 | 3 |
| 3 | 2 | 99 ± 21 | 0.5 | 0.5 ± 0.1 | 3 |
| 4 | 5 | 790 ± 120 | 0.5 | 0.2 | 3 |
| 5 | 10 | 880 ± 100 | 0.5 | 0 | 3 |
| 6 | 15 | 1200 ± 240 | 0.5 | 0.1 | 3 |
| 7 | 25 | 2000 ± 120 | 0.5 | 0.24 | 3 |
| 8 | 30 | 2000 ± 120 | 0.5 | 0.2 ± 0.1 | 10 |
| 9 | 40 | 940 ± 100 | 0.6 | 0 | 3 |
| 10 | 50 | 380 ± 170 | 0.5 | 0.24 | 2 |
| 11 | 60 | 420 ± 4 | 0.5 | 0.6 | 3 |
| 12 | 75 | 200 ± 24 | 0.6 | 0.7 ± 0.03 | 3 |
| 13 | 80 | 170 ± 2 | 0.6 | 0.1 | 3 |
| 14 | 100 | 500 | 0.5 | 1 ± 0.2 | 2 |

*N is the number of experiments performed.

Examples 2–14 demonstrate that the flux of water through the membrane can be significantly altered by changing the concentration of the substrate in an inert solvent in the hydrophobic liquid in the support membrane. For example, water flux varied by over an order of magnitude in going from 2% olive oil to 30% olive oil in the membrane.

EXAMPLES 15–20

Water Flux Can be Altered by Changing Concentration of Hydrophobic Liquid

Example 1 was repeated except that various concentrations of tricaprylin (TC) dissolved in squalene were loaded into the support membrane. The differences in flux and time lag for different concentration of tricaprylin in squalane is given in Table 3.

TABLE 3

The Effect of different Concentrations of Hydrophobic Liquid (tricaprylin (TC)) on Water Flux and Time Lag. (All values based on three experiments).

| Ex. No. | Percent TC in Squalane | Water Flux (mg/cm$^2$/hr) | Control (mg/cm$^2$/hr) | Time Lag (hrs) |
|---|---|---|---|---|
| 15 | 5 | 13 ± 10 | 0.5 | 0.10 ± 0.1 |

TABLE 3-continued

The Effect of different Concentrations of Hydrophobic Liquid (tricaprylin (TC)) on Water Flux and Time Lag. (All values based on three experiments).

| Ex. No. | Percent TC in Squalane | Water Flux (mg/cm²/hr) | Control (mg/cm²/hr) | Time Lag (hrs) |
|---|---|---|---|---|
| 16 | 10 | 100 ± 5 | 0.4 | 0.21 ± 0.02 |
| 17 | 15 | 380 ± 13 | 0.5 | 0.23 ± 0.02 |
| 18 | 25 | 790 ± 40 | 0.5 | 0.25 |
| 19 | 50 | 480 ± 80 | 0.5 | 0.04 |
| 20 | 100 | 710 ± 10 | 0.6 | 0.50 ± 0.1 |

Examples 15–20 demonstrate that dissolving another hydrophobic liquid (i.e. tricaprylin), in an inert solvent has a similar effect on water flux and time lag as that seen with solutions of olive oil.

EXAMPLES 21–27

Use of Various Triglyceride Oils as the Hydrophobic Liquid in Membranes

Example 1 was repeated, except that other triglyceride oils were loaded into the support membrane. All are naturally occurring oils, with the exception of tricaprylin, the glycerol triester of caprylic acid ($CH_3(CH_2)_6COOH$). The results are summarized in Table 4. Each of these triglyceride oils is hydrolyzed by PPL, and the water flux in the presence of the enzyme is much greater (at least 100 times) than in the absence of PPL.

TABLE 4

Effect of Various Triglycerides on Water Flux and Time Lag in Accurel A3 Membrane

| Ex No. | Oil | Flux (mg/cm²/hr) | Control (mg/cm²/hr) | Time Lag (hrs) | N |
|---|---|---|---|---|---|
| 21 | Tricaprylin | 710 ± 10 | 0.5 | 0.5 ± 0.1 | 3 |
| 22 | Safflower Oil | 540 ± 114 | 0.5 | 0.6 ± 0.1 | 3 |
| 23 | Olive oil | 500 ± 26 | 0.5 | 1.0 ± 0.2 | 6 |
| 24 | Palm oil | 114 ± 52 | 0.5 | 2.4 ± 0.3 | 3 |
| 25 | Coconut oil | 460 ± 30 | 0.5 | 4.0 ± 0.0 | 2 |
| 26 | Cocoa Butter | 60 ± 5 | 0.5 | 6.0 ± 2.0 | 3 |
| 27 | Triolein | 220 ± 13 | 0.5 | 0.6 ± 0.1 | 3 |

All experiments were performed with 7 mg/ml PPL in intestinal buffer (pH 7.5) containing 0.2 wt % bile extract. Substrates were loaded into an Accurel A3 membrane. Reaction temperature was 37°.

Examples 21–27 demonstrate that different triglyceride oils can be immobilized in the support membrane to form a membrane, and that the nature of the oil can change the flux and time lag through the membrane, once the trigger has been encountered.

EXAMPLES 28–31

With PPL as Triggering Agent, Water Flux and Time Lag are not Dependent on PPL Concentration Example 1 was repeated, except that tricaprylin was loaded in the support membrane and various concentrations of PPL were tested. The water flux is similar in all cases and, except for the very low PPL concentrations (which had longer time lag), the performance of the membrane was independent of PPL concentrations.

TABLE 5

Effect of Enzyme Concentration on Lag Time and Water Flux Through Tricaprylin Membranes. (Receptor solutions are intestinal buffer containing enzyme and 0.2 wt % bile salts)

| Ex. No. | Enzyme Concentration (mg/ml) | Time Lag (hrs) | Water Flux (mg/cm²/hr) | N |
|---|---|---|---|---|
| 28 | 0.1 | 2.3 ± 0.2 | 450 ± 40 | 3 |
| 29 | 1.0 | 0.5 ± 0.1 | 660 ± 67 | 3 |
| 30 | 5.0 | 0.5 ± 0.1 | 710 ± 10 | 3 |
| 31 | 10.0 | 0.5 ± 0.0 | 690 ± 44 | 3 |

Examples 28–31 demonstrate that, above a threshold of 1.0 mg/ml enzyme, the concentration of PPL does not affect the water flux and time lag of water through a tricaprylin membrane. This is an important consideration for a lipase-triggered controlled release device, since it indicates that variations in PPL concentration do not greatly alter the water flux behavior through the membrane.

EXAMPLE 32

Use of Non-Triglyceride Hydrophobic Liquids

Example 1 was repeated except a hydrophobic liquid that is not a triglyceride (triesters of glycerol) was used. Caprylic anhydride, $(CH_3(CH_2)_6CO)_2O$, in squalene (2:8, V:V) was loaded in an Accurel membrane disk, and the water flux and time lag determined as before. Steady state flux was 275±10 mg/cm²/hr and the time lag was 0.4 hours, whereas in the control experiment with no enzyme, the water flux was 0.7 mg/cm²/hr.

Example 32 illustrates that hydrophobic liquids that are not triesters of glycerol can be used in SLM membranes when the triggering agent is pancreatic lipase.

EXAMPLES 33–35

*Candida cylindracea* Lipase (CCL) as Triggering Substance

Example 1 was repeated, except the lipase enzyme from *Candida cylindracea* (also called *Candida rugosa*) was used as the triggering agent, at different concentrations. Olive oil was loaded in Accurel A3 membrane, and the membrane was fitted in the weight gain device as above.

TABLE 6

Water Flux Through Olive Oil Membrane in the Presence of *Candida cylindracea* Lipase (CCL)

| Ex. No. | Enzyme Concentration (mg/ml) | Water Flux (mg/cm²/hr) | Control (mg/cm²/hr) | Time Lag (hrs) |
|---|---|---|---|---|
| 33 | 0.14 | 8 | 0.6 | <10 |
| 34 | 1.4 | 340 | 0.6 | 2.4 |
| 35 | 14 | 526 | 0.6 | 1.5 |

Examples 33–35 demonstrate that the lipase from the yeast *Candida cylindracea* is capable of triggering water flux through a membrane. They also demonstrate that in the 1 to 10 mg/ml concentration range, water flux and time lag are not strongly dependent on CCL concentration.

EXAMPLES 36–37

The Use of Other Lipases as Triggering Agents, With Triglycerides as Hydrophobic Liquids Example 1 was repeated except that lipases from Mucor species (Lipase MAP, Amano Enzymes, Troy, Va.) and *Rhizopus iavanicus* (Lipase FAP, Amano Enzymes, Troy, Va.) were used as triggering substances. The receptor solution in these experiments did not contain bile salts.

TABLE 7

Water Flux Through Olive Oil Membranes in the Presence of Other Lipases. (Olive Oil loaded in Accurel A3 membrane. 7 mg/ml enzyme, intestinal buffer, no bile salts.)

| Ex. No. | Enzyme | Time Lag (hrs) | Flux (mg/cm²/hr) | Control (mg/cm²/hr) | N |
|---|---|---|---|---|---|
| 36 | FAP | 2.7 ± 0.2 | 38 ± 2 | 0.6 | 2 |
| 37 | MAP | 2.6 ± 0.2 | 23 ± 6 | 0.5 | 2 |

Examples 36–37 demonstrate that other lipases are capable of triggering water permeability through porous membranes having entrained olive oil.

EXAMPLES 38–40

The Use of Other Lipases as Triggering Agents With Non-triglyceride Hydrophobic Liquids Example 1 was repeated except that a non-triglyceride hydrophobic liquid (caprylic anhydride) was used and lipases other than pancreatic lipase were used as the triggering substance. These lipases were Lipase P (from *Pseudomonas* sp., Amano Enzymes, Troy, Va.); Lipase OF (from *Candida cylindracea*, Meito Sangyo, Tokyo, Japan); Lipase, AY (from *Candida cylindracea*, Amano Enzymes, Troy, Va.).

TABLE 8

Water Flux Through Caprylic Anhydride Membranes in the Presence of Microbial Lipases. (20 vol % Caprylic Anhydride/Squalane in Accurel A3 membrane. 5 mg/ml enzyme, intestinal buffer, 0.2 wt % bile salts.)

| Ex. No. | Enzyme | Time Lag (hrs) | Flux (mg/cm²/hr) | Control (mg/cm²/hr) | N |
|---|---|---|---|---|---|
| 38 | Lipase P | 0.1 | 422 ± 30 | 0.5 | 2 |
| 39 | Lipase AY | 0.7 | 46 ± 12 | 0.6 | 2 |
| 40 | Lipase OF | 0.2 | 104 | 0.5 | 1 |

Examples 38–40 demonstrate that lipases other than pancreatic lipase can trigger water permeability through membranes where the hydrophobic liquid is not a triglyceride.

EXAMPLE 41

Pig Liver Esterase Triggered Membrane

Example 1 was repeated with 50% ethyl caprylate, $CH_3(CH_2)_6COOCH_2CH_3$, dissolved in squalane loaded in the support membrane. The receptor solution was intestinal buffer containing 20 μl/ml (100 unites) pig liver esterase. The water flux was measured to be 400 mg/cm²/hr and the time lag was 0.8 hours. In the control reaction without enzyme, the flux was 1.1 mg/cm²/hr.

Example 41 demonstrates that an esterase enzyme present in the liver of most mammals, can be used to trigger water permeability.

EXAMPLES 42–43

Protease-Triggered Membrane

Example 1 was repeated with a mixture of N-tert-butyloxycarbonyl-L-phenylalanine 1-octyl ester, N-tert-butyloxycarbonyl-L-phenylalanine 2-octyl ester, and N-tert-butyloxycarbonyl-L-phenylalanine 3-octyl ester loaded into a disk of Celgard 2400 membrane (polypropylene membrane, 25 μm thick, 40% porosity, Hoechst-Celanese, Charlotte, N.C.). The receptor solution for these experiments was 0.125M phosphate buffer, pH 7.5, containing various amounts of chymotrypsin. Results are presented in Table 9.

TABLE 9

Chymotrypsin-Triggered Membrane

| Ex. No. | Enzyme Concentration (mg/mL) | Time Lag (hrs) | Water Flux (mg/cm²/hr) | Control (mg/cm²/hr) |
|---|---|---|---|---|
| 42 | 10 | 2.4 | 127 | 2 |
| 43 | 1 | 2.6 | 120 | 2.1 |

Examples 42–43 demonstrate that a protease, chymotrypsin, can trigger water permeability in membranes.

EXAMPLES 44–50

Various Support Membranes Can Be Used

Example 1 was repeated except that different commercially available membranes were used as the support membrane. Properties of the membranes are summarized in Table 10.

TABLE 10

Properties of Commercially Available Membranes

| Membrane | Material | Thickness (μm) | Pore Size (μm) |
|---|---|---|---|
| Celgard 2400 | polypropylene | 25 | 0.02 |
| Celgard 2500 | polypropylene | 25 | 0.04 |
| Accurel 1E | polypropylene | 120 | 0.1 |
| UF Membrane[1] | Polysulfone | 100 | 0.1 |
| Accurel A3(2E) | polypropylene | 150 | 0.2 |
| Kynar | PVDF | 120 | 0.22 |
| Whatman[2] | PTFE | 150 | 0.5 |

[1].) Millipore Corp., Bedford, MA.
[2].) Whatman Co. Clifton, NJ.

TABLE 11

Water Fluxes and Time Lags Through Membranes Loaded With Olive Oil In the Presence of Porcine Pancreatic Lipase. (All receptor solutions contained 7 mg/ml PPL, 0.2% bile softs, pH 7.5)

| Ex. No. | Membrane | Time Lag (hrs) | Flux (mg/cm²/hr) | Control (mg/cm²/hr) | N |
|---|---|---|---|---|---|
| 44 | Celgard 2400 | 0.5 ± 0.1 | 180 ± 16 | 1.2 ± 0.2 | 2 |
| 45 | Celgard 2500 | 0.9 ± 0.1 | 430 ± 20 | 2.2 ± 0.1 | 2 |
| 46 | Accurel 1E | 2.4 ± 0.2 | 290 ± 5 | 0.5 ± 0.1 | 3 |
| 47 | UF Membrane | 1.4 | 800 | 4.8 | 1 |

TABLE 11-continued

Water Fluxes and Time Lags Through Membranes Loaded With Olive Oil In the Presence of Porcine Pancreatic Lipase. (All receptor solutions contained 7 mg/ml PPL, 0.2% bile softs, pH 7.5)

| Ex. No. | Membrane | Time Lag (hrs) | Flux (mg/cm²/hr) | Control (mg/cm²/hr) | N |
|---|---|---|---|---|---|
| 48 | Accurel A3 | 0.5 ± 0.1 | 500 ± 25 | 1.0 ± 0.3 | 2 |
| 49 | Kynar | 0.4 ± 0.1 | 240 ± 20 | 0.6 ± 0.1 | 3 |
| 50 | Whatman | 0.1 | 1900 | 2.4 | 1 |

Examples 44–50 demonstrate that hydrophobic membranes made of different materials can be used as support membranes.

EXAMPLES 51–53

Membranes Constructed With Cast Kynar Films as the Support Membrane

Example 1 was repeated using membranes consisting of cast, porous Kynar films, the pores of which were loaded with olive oil.

A 15-wt % solution of Kynar 460(PVDF) in DMF was cast on glass plates. The thickness of cast membranes was adjusted using a spreading knife. A microporous membrane was formed from the cast solution by quenching in water. The membrane was dried overnight, and a disk of material was cut and loaded with olive oil.

TABLE 12

SLM Membranes Constructed from Kynar Films

| Ex. No. | Thickness (μm) | Water Flux (mg/cm²/hr) | Control (mg/cm²/hr) | Time Lag (hrs) |
|---|---|---|---|---|
| 51 | 13 | 160 ± 13 | 1.2 | 0.25 |
| 52 | 33 | 51 ± 0.9 | 0.75 | 2 |
| 53 | 57 | 4 ± 0.3 | 0.80 | >20 |

Examples 51–53 demonstrate that cast Kynar films can be used as the support membrane.

EXAMPLE 54 AND 55

Heat (and Enzyme) Triggered Membrane

Example 1 was repeated except that the support membrane was loaded with melted palm oil. This oil is a solid at room temperature (25° C.) and a liquid at 45° C. Lipase-catalyzed hydrolysis of solid substrates is extremely slow, so that the temperature of the receptor solution must be above the melting temperature of palm oil (40° C.) and the lipase must be present for water permeability to be triggered.

TABLE 13

Temperature Behavior of Membranes Loaded with Palm Oil. (Three experiments each)

| Ex. No. | Temperature | Time Lag (hrs) | Water Flux (mg/cm²/hr) | Control (mg/cm²/hr) |
|---|---|---|---|---|
| 54 | 25 | 2.0 | 3.3 ± 0.3 | 0.5 |
| 55 | 45 | 2.0 | 303 ± 3 | 3.7 ± 0.6 |

Examples 54–55 demonstrate that a membrane can be constructed that is triggered by the dual triggers of elevated heat and the presence of lipase. The mechanism is based on the fact that the enzyme reacts slowly or not at all with the solid oil (which has a melting temperature of 40° C.), but will react with the liquid oil.

EXAMPLES 56 AND 57

Heat Triggered Membrane With Incorporated Enzyme

An Accurel membrane disk was loaded with melted palm oil in which 2 mg/ml PPL had been suspended. The membrane was rapidly cooled to solidify the oil, then fitted into a weight-gain device, and the water flux through the membrane at 25° C. and 45° C. determined. The results are presented in Table 14.

TABLE 14

Heat Activated Membranes

| Ex. No. | Temperature (°C.) | Time Lag (hrs) | Water Flux (mg/cm²/hr) |
|---|---|---|---|
| 56 | 25 | not measurable | 1.3 |
| 57 | 45 | 2.0 | 68 |

Examples 56–57 demonstrate that a membrane can be made that is activated by heat alone, since the required enzyme is immobilized in the membrane along with the hydrophobic liquid.

EXAMPLES 58–61

Nucleophile Triggered Membrane

In these examples, the triggering agent is a chemical species, not an enzyme. Support membranes are loaded with 20% caprylic anhydride in squalane. The receptor solutions consist of the respective nucleophiles at the given pH and concentration.

TABLE 15

Nucleophile Triggered Water Permeability. (All values based on three experiments.)

| Ex. No. | Nucleophile | Water Flux (mg/cm²/hr) | Control (mg/cm²/hr) | Time Lag (hrs) |
|---|---|---|---|---|
| 58 | Hydrazine, 1M, pH 10 | 25 ± 14 | 0.75 | 0.5 |
| 59 | Hydroxylamine, 1M, pH 10 | 39 ± 5 | 0.6 | 0.5 |
| 60 | Hydroxylamine, 0.1M, pH 10 | 24 | 0.75 | 0.2 |
| 61 | Ammonia, 1M NH₄Cl, pH 10 | 2.1 ± 0 | 0.4 | 0.5 |

In Examples 58–61 the triggering agent is a non-enzymatic chemical. These examples demonstrate that it is possible to construct a membrane where the triggering agent is not an enzyme.

EXAMPLE 62

Reducing Agent Triggered Membrane

Example 1 was repeated except that the hydrophobic liquid in the support membrane consisted of 20% dilauryl peroxide, $(CH_3(CH_2)_{10}COO)_2$, in ethyl caprylate. The triggering agent consisted of sodium borohydride (1M NaBH₄, pH 10). The water flux was 90±10 mg/cm$^2$/hr (three experiments) and the time lag was too small to be accurately measured. In the control experiment without sodium borohydride, the water flux was 13 mg/cm$^2$/hr. This is another example of chemical reaction triggered permeability. The borohydride reduces the peroxide to two molecules of lauric acid, $CH_3(CH_2)_{10}COOH$, and this molecule facilitates water transport through the membrane.

EXAMPLES 63–65

Demonstration of Membrane in Controlled Release Device: Membrane Pouch

Membrane pouches were constructed from two disks of flat-sheet support membrane. Pouches were made from commercially available flat-sheet membranes.

Two flat sheets of membrane were sandwiched around a sheet of low-density polyethylene that had a large hole, forming a chamber between the sheets of membrane. A Mylar tab was placed between one membrane disk and the polyethylene sheet to form a filling hole for the pouch. The assembly was pressed between the heated surfaces of a T-shirt press, which melted the polyethylene, cementing together the two membrane disks.

Trimmed pouches were filled with Waterlock J-500, containing 5% dextran blue as an indicator dye used to detect leaks, and the filling hole was heat sealed. The pores of the membrane were filled with olive oil. Water flux into the pouch was determined by weight gain. Controls with no enzyme in the receptor solution were run in parallel.

Three types of flat-sheet membrane were tested: Accurel A3, Celgard 2400, and Gore-Tex (W. L. Gore Assoc., Elkton, Md.). Gore-Tex is a polytetrafluorethylene (PTFE) membrane, 25 μm thick, with 0.2-μm pores.

TABLE 16

Water Flux into Olive Oil Membrane Pouches

| Ex. No. | Membrane Material | Pore Size (μm) | Water Flux (mg/cm$^2$/hr) Control | Lipase |
|---|---|---|---|---|
| 63 | Celgard 2400 | 0.02 | 1.4 ± 0.1 | 87 ± 2.9 |
| 64 | Accrel | 0.2 | 0.5 ± 0.02 | 64 ± 5 |
| 65 | Gore-Tex | 0.2 | 21 ± 7 | 65 ± 3 |

In Examples 63–65, membrane pouches were constructed as models for controlled release devices in which an active core is covered and protected from water by a SLM membrane. These results demonstrate that such pouches could be constructed from Celgard, Accurel, and Gore-Tex membranes.

EXAMPLES 66 AND 67

Membrane Capsules

Capsule bodies were formed from hydrophobic, microporous membranes. The pores of these membranes were filled with the hydrophobic liquid. The capsules were filled with a core material that contained an osmotic attractant and that expanded in the presence of water. In the presence of the enzyme, water was transported across the membrane, the core expanded, and eventually the capsule burst, releasing the drug. Hydrophobic membrane capsules were made of two materials: polyethylene and Kynar.

Polyethylene (PE) membranes were formed by a thermal phase inversion process (Strathmann, H., "Production of Microporous Media by Phase Inversion Processes," in *Materials Science of Synthetic Membranes*, D. R. Lloyd (ed.). American Chemical Society, Washington, D.C. (1985) p. 165.). The polymer was melted in the presence of diluent. The temperature was lowered, and the polymer phase separated. Using a mandrel as a solid substrate, the polymer precipitated forming a microporous membrane in the shape of a half-capsule.

A suspension of 17% PE (Tenite 808A low density PE, Eastman Chemicals, Kingsport, Tenn.) and 0.085% talc (a nucleating agent) in olive oil was heated to 160° C. with stirring. Mandrels were dipped in this solution, withdrawn, then dipped in liquid nitrogen to precipitate the polymer. Olive oil in the polymer was exchanged by dipping in acetone. Capsules were then removed from the mandrels and treated with olive oil.

Kynar membranes were formed by a similar process. A suspension of 15% Kynar 461 PVDF in propylene carbonate was made and heated to approximately 120° C. with stirring, until the Kynar melted. Mandrels were dipped in the solution, then quenched in liquid nitrogen. The remaining propylene carbonate was exchanged out with ethanol. Capsules were then removed from the mandrels and treated with olive oil.

Waterlock J-500 or Waterlock containing 10% acid black as a model drug were used as core formulations in the capsules.

Half-capsules were cast with slightly different inner diameters, to form bodies and caps for the capsules. The capsules were loaded with core formulations as fully as possible, and cap and body joined and sealed with a solution consisting of 15% cellulose acetate (CA 398-10, Eastman Chemical, Kingsport, Tenn.), 56.9% acetone, 28% ethanol, and 0.1% Coomassie Blue.

Water flux was measured by determining the weight gain of the capsule. Capsules were filled with the core formulation, glued to a stiff wire attached to the pan hook of an analytical balance, then partially immersed in test solution.

Capsules were suspended in receptor solutions, which included intestinal buffer with and without lipase. The balance was tared at time zero, and the weight gain of the suspended capsule determined. Capsules were tested first for 2 to 4 hours in intestinal buffer without lipase to test for leaks in the membrane, then transferred to a lipase solution.

To test water flux through the membrane, half-capsules were tested. The capsules were tested loaded with olive oil in the absence of lipase, and loaded with olive oil in the presence of lipase.

TABLE 17

Water Fluxes into Capsules

| Ex. No. | Membrane | Water Flux (mg/cm$^2$/hr) Control | Lipase |
|---|---|---|---|
| 66 | Polyethylene | 0.27 ± 0.2 [40] | 6.3 ± 2.2 [48] |
| 67 | Kynar | 0.4 ± 0.4 [3] | 2.9 ± 0.5 [3] |

[ ] indicates number of test runs.

Examples 66–67 demonstrate that a capsule can be formed from support membrane material.

EXAMPLES 68–70

Membrane Coated Tablets

Tablet cores were coated with microporous Kynar membranes, which served as the support for the immobilized-liquid membrane. Cores consisted of 40% Ac-Di-Sol, 42%

Avicel, 10% Biogel P-6 polyacrylamide beads (Biorad, Calif.) (hydrolyzed), 7% Pseudoephedrine and 1% acid black. To prevent the immobilized oil or the coating solvents from interacting with the core material, a sugar coating was placed around the core. The sugar coating consisted of a mixture of 53.3 vol % sugar, 27.7 vol % water and 20 vol % light corn syrup, stirred to dissolve, then heated to a low boil without stirring to a temperature of 149° to 154° C. Wires were attached to tablet cores by epoxy, then coated with the sugar mixture. These cores were coated by two methods 1) dip-coating, or 2) spray-coating.

Dip-Coating

To dip-coat, sugar-coated tablet cores attached to wires were dipped in a solution of Kynar 461 PVDF (10.8 wt %) and n-propanol (15.7 wt %) in acetone. Three to five coats were applied by dipping, and the acetone was allowed to evaporate after each coating. Olive oil was absorbed into the pores between each coat. After the final coat had dried, remaining olive oil was exchanged out by dipping the tablet repeatedly in hexane, then allowing it to dry. Dry membranes were 90 to 240 µm thick, as measured by scanning electron microscopy.

Spray Coating

For spray-coating, the wires were cut from sugar-coated tablet cores, and the cores were coated with microporous Kynar PVDF coatings in a pan-coater using a commercial air-brush. A Kynar (9 wt %) solution in acetone containing 16 wt % n-propanol was sprayed on the cores through an air-brush from a distance of approximately 4 inches. Air pressure to the air brush was 20 psi. The tablets were washed with hexane and dried. Dry membranes were 50 to 90 µm thick, as measured by scanning electron microscopy.

Coated tablets were immersed in olive oil for 5 to 30 minutes, until the entire coating became translucent. The tablets were removed and blotted to remove excess oil.

Controlled-Release Tests

Coated tablets loaded with olive oil were immersed for 1 to 25 hours in intestinal buffer containing bile salts without enzyme. Tablets were transferred to 0.125M phosphate buffer (pH 7.5), 0.2 wt % bile salt, containing 7 mg/ml lipase. The time required for the membrane coating to burst after immersion in the lipase solution was determined.

TABLE 18

Burst Times For Tablets with Highly Expandable Cores

| Ex. No. | Fabrication Method | Time in Control (hrs) | Burst Time* (hrs) | N |
|---|---|---|---|---|
| 68 | Dip | 1–2.5 | 4.8 ± 1.4 | 8 |
| 69 | Dip | 8–25 | 4.9 ± 1.5 | 18 |
| 70 | Spray | 23 | 6.2 ± 0.8 | 8 |

*Time the tablet burst open after being placed in lipase solution.

Examples 68–70 demonstrate that a Kynar PVDF coating which is a suitable support membrane can be laid down on a tablet core, and that this membrane prevents the tablet from opening until lipase is encountered. In these examples the core contained a material which swelled in the presence of water. When the triggering agent causes water to permeate the coating, the core swells, bursting the tablet.

EXAMPLE 71

Membrane Coated Tablets—Fluid-Bed Coater

Tablet cores consisting of 5 wt % Ac-Di-Sol (a crosslinked form of carboxy-methyl-cellulose, FMC Corp., Philadelphia, Pa.), 40.5 wt % Avicel (FMC, microcrystalline cellulose), 40.5 wt % lactose, and 14 wt % pseudoephedrine HCl were pressed in a hand-operated tablet press.

The cores were coated with a pre-coat of 5% sucrose, 5% methocel (hydroxypropyl methylcellulose, Dow, Midland, Mich.) in water with a fluidized bed coater (STREA-1). The cores were then sprayed with a solution of 3% Kynar in acetone containing 9.5% water. The tablets were sprayed until they had gained 20 mg weight on average and a thickness of 66 µm. Porosity of the Kynar coating was 40%.

The tablets were placed in tricaprylin for 16 hours to load the cores with the liquid, then wiped off. Nine tablets were placed in a 0.1M phosphate buffer solution (pH 7.5) containing 0.2 wt % bile salt extract for two hours. Six tablets were transferred to a similar solution containing 5 mg/ml PPL. The burst time for the tablets exposed to enzyme was 6.0±0.6 hours, while the tablets in solution without enzyme did not burst in 48 hours.

Figure 3:
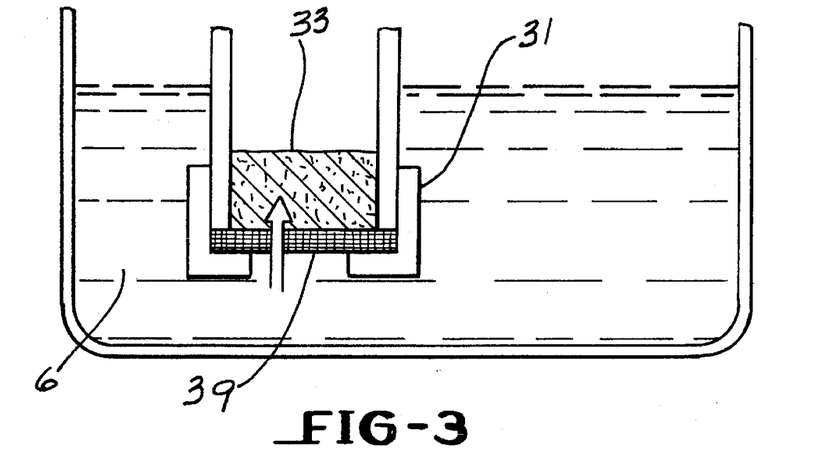
FIG. 3 is a schematic of a weight gain test apparatus used in testing devices of this invention.
Figure 4:
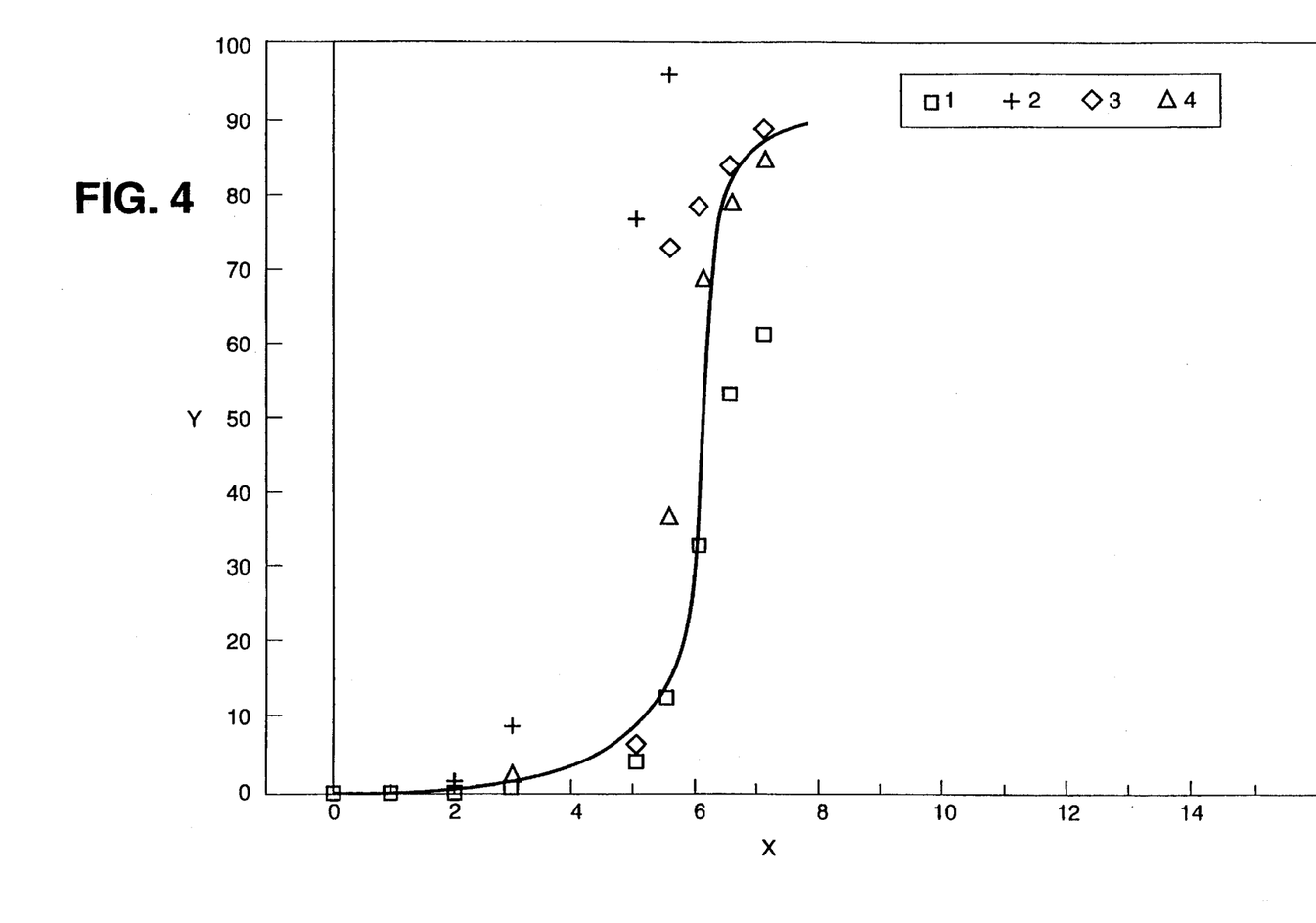
FIG. 4 is a graph of the quantity of pseudoephedrine released as a function of time for exemplary devices of this invention.

The receptor solution was analyzed by HPLC for release of pseudoephedrine. Essentially all of the poseudoephedrine was released within 1 hour after the tablets burst open. No release of drug was detected from tablets that did not burst open. The release profile for the four tablets exposed to enzyme is presented in FIG. 3 where the quantity (percent) of pseudoephedrine released (Y) is plotted as a function of time in hours (X).

Example 71 demonstrates that tablet cores which expand in water (due to the Ac-Di-Sol component) can be coated with an activated coating. Tablets coated with this membrane, in the presence of physiological concentrations of pancreatic lipase, will burst open in a predictable time, while the tablets in solution without enzyme are inert, and do not burst open.

EXAMPLE 72

Tablets Triggered by Pig Liver Esterase

Tablets prepared as in the previous example were loaded with ethyl caprylate. Four tablets were placed in a 0.1M phosphate buffer solution (pH 7.5) containing 2 mg/ml pig liver esterase, Four tablets were also placed in similar solution without enzyme. The burst time for the tablets in enzyme solution was 28 hours, while the tablets in solution without enzyme did not burst in 48 hours.

Example 72 demonstrates that a triggered release device can be formulated that is triggered by another enzyme other than a lipase; in this case, a liver esterase.

EXAMPLE 73–75

Burst Times are Independent of Time in Solution Without Lipase

Tablets prepared as in Example 71 were loaded with olive oil and placed in receptor solution (0.125M phosphate, pH 7.5, 0.2 wt % bile salts) without enzyme for various times, then transferred to receptor solution containing 5 mg/ml PPL. The burst times, as indicated in Table 19, did not show a dependence on the time in buffer solution before exposure to the enzyme.

TABLE 19

Effect of Intestinal Buffer Exposure on Burst Time of Tablets

| Ex. No. | Buffer Exposure Time (hrs) | Burst Time (hrs) | N |
|---|---|---|---|
| 73 | 0 | 5.5 ± 0.3 | 6 |
| 74 | 2 | 6.0 ± 0.04 | 6 |
| 75 | 9 | 4.3 ± 1.0 | 6 |

Examples 73–75 demonstrate the exposure to intestinal buffer and bile salt without enzyme does not cause early bursting of the tablets.

EXAMPLES 76 AND 77

Burst Times Are Dependent on Hydrophobic Liquid

Tablets prepared as above were loaded with two different oils: olive oil and tricaprylin. The two sets of tablets were then placed in receptor solutions containing intestinal buffer with 0.2 wt % bile salt extract. After 2 hours, the tablets were transferred to similar solution containing 5 mg/ml PPL. Burst times for each set are presented in Table 20. With both sets, tablets left in buffer without enzyme did not burst in the 48 hours of the test.

TABLE 20

Effect of Hydrophobic Liquid on Burst Times of RTP Tablets

| Ex. No. | Hydrophobic Liquid | Burst Time | N |
|---|---|---|---|
| 76 | Tricaprylin | 5.4 ± 0.8 | 6 |
| 77 | Olive Oil | 9.5 ± 0.4 | 3 |

Parallel to the case using flat sheets, where changing the hydrophobic liquid in the membrane could change the water flux, changing the hydrophobic liquid in the coating on the tablets changes the burst time. This is important for site-selective drug delivery. Unlike duodenum transit, intestinal transit is fairly constant. If the tablet can be formulated to burst reproducibly at some time after leaving the duodenum and encountering lipase, then the tablet should burst in about the same position in the ileum each time.

We claim:

1.) A device for dispensing a beneficial agent to an aqueous environment comprising:
 a.) a hydrophilic formulation comprising a beneficial agent;
 b.) a wall that surrounds said hydrophilic formulation, said wall formed at least in part of a microporous hydrophobic support membrane; and
 c.) a hydrophobic liquid entrained within said pores of said microporous support membrane, the permeability of the hydrophobic liquid to water is less than $9 \times 10^{-6}$ cc STP-cm/cm$^2$-sec-cmHg and said hydrophobic liquid being capable of change such that the permeability to water changes at least an order of magnitude.

2.) The device as recited in claim 1 wherein said hydrophobic liquid has a solubility in water of less than 15% and said hydrophobic liquid forms a contact angle of less than 90° with the microporous hydrophobic support membrane material.

3.) The device as recited in claim 2 wherein said support membrane has a water contact angle greater than 50°, said support membrane has a permeability to water of less than $9 \times 10^{-6}$ cc STP-cm/cm$^2$-sec-cmHg, said support membrane has a pore size less than 100 μm and said support membrane has a thickness of 1 μm to 1 mm.

4.) The device as recited in claim 3 wherein said hydrophobic liquid is capable of changing such that the permeability to water changes at least an order of magnitude following exposure to a predetermined enzyme.

5.) The device as recited in claim 4 wherein said hydrophobic liquid is a triglyceride, a fatty anhydride, a fatty acid ester of cholesterol, a fatty acid peroxide, a polyester, a long chain ester having the formula $CH_3(CH_2)_g COO(CH_2)_h CH_3$ where g and h are independently from 2 to 24, a hydrophobic dipeptide, a hydrophobic amino acid ester or a disulfide with an optional inert solvent.

6.) The device as recited in claim 5 wherein said membrane is polyalkene, polyhaloalkene, cellulose ester, polycarbonate, polystyrene, polyvinyl ester, polyvinyl ether, polysiloxane, polyacrylate, polyamide or polyether.

7.) The device as recited in claim 6 wherein said membrane is polypropylene, polyethylene or polyvinylidene fluoride.

8.) The device as recited in claim 6 wherein said hydrophilic formulation includes an osmotic agent or a swellable component.

9.) The device as recited in claim 6 wherein such device is capable of releasing the beneficial agent following exposure to the predetermined enzyme, in the duodenum.

10.) The device as recited in claim 6 wherein such device is capable of releasing the beneficial agent, following exposure to the predetermined enzyme, in the ileum.

11.) The device as recited in claim 6 wherein such device is capable of releasing the beneficial agent, following exposure to the predetermined enzyme, in the colon.

12.) The device as recited in claim 6 wherein said device is capable of releasing the beneficial agent, following exposure to the predetermined enzyme, in the jejunum.

13.) The device as recited in claim 6 in the form of a tablet, capsule or bead.

14.) The device as recited in claim 1 wherein said porous membrane is a polyvinylidene fluoride or a polyalkene with a triglyceride entrained therein.

15.) The device as recited in claim 14 wherein the triglyceride is a 20% to 100% solution of triolein, olive oil or tricaprylin in squalene.

16.) The device as recited in claim 1 wherein said porous membrane is a polyvinylidene fluoride or a polyalkene and said hydrophobic liquid is ethylcaprylate or 15% to 25% solution of octanoyl-L-phenylalanine in ethyl caprylate.

17.) The device as recited in claim 1 wherein said porous membrane is polyalkene, polypropylene, polyethylene or polyvinylidene fluoride and the hydrophobic liquid is a mixture of N-tert-butyl-oxycarbonyl-L-phenylalanine-1-octyl ester, N-tert-butyl-oxycarbyl-L-phenylalanine-2-octyl ester and N-tert-butyl-oxycarbonyl-L-phenylalanine-3-octyl ester.

18.) The device as recited in claim 3 wherein said hydrophobic liquid is capable of changing such that the permeability to water changes at least an order of magnitude following exposure to heat.

19.) The device as recited in claim 3 wherein said hydrophobic liquid is capable of changing such that the permeability to water changes at least an order of magnitude following exposure to light.

20.) The device as recited in claim 3 wherein said hydrophobic liquid is capable of changing such that the permeability to water changes at least an order of magnitude following exposure to a non-enzymatic chemical.

21.) A method for the controlled delivery of a beneficial agent to an aqueous environment of use which comprises placing the device of claim 1 into the aqueous environment of use.

* * * * *